United States Patent
James, III et al.

(10) Patent No.: US 9,585,548 B2
(45) Date of Patent: Mar. 7, 2017

(54) OPTICAL ELEMENT FOR MIE SCATTERING LIGHT FROM AN OPTICAL FIBER

(71) Applicant: SCHOTT CORPORATION, Elmsford, NY (US)

(72) Inventors: William H. James, III, South Abington Township, PA (US); Elizabeth Chase, Clarks Summit, PA (US); Mark J. Davis, Clarks Summit, PA (US); Paula Vullo, Harding, PA (US); Sally Pucilowski, Duryea, PA (US); Eric Hector Urruti, Duryea, PA (US)

(73) Assignee: SCHOTT CORPORATION, Elmsford, NY (US)

( * ) Notice: Subject to any disclaimer, the term of this patent is extended or adjusted under 35 U.S.C. 154(b) by 0 days.

(21) Appl. No.: 13/796,397

(22) Filed: Mar. 12, 2013

(65) Prior Publication Data
US 2014/0270639 A1    Sep. 18, 2014

(51) Int. Cl.
*G02B 6/00*    (2006.01)
*A61B 1/00*    (2006.01)
(Continued)

(52) U.S. Cl.
CPC .......... *A61B 1/00165* (2013.01); *C03C 3/089* (2013.01); *C03C 3/093* (2013.01);
(Continued)

(58) Field of Classification Search
CPC .............................. G02B 6/004; G02B 6/0016
See application file for complete search history.

(56) References Cited

U.S. PATENT DOCUMENTS

| | | |
|---|---|---|
| 2,106,744 A | 2/1938 | Hood et al. |
| 3,549,524 A | 12/1970 | Haller |
| | (Continued) | |

FOREIGN PATENT DOCUMENTS

WO    2013010019    1/2013

OTHER PUBLICATIONS

Y. Kawamoto et al., "Prediction of Immiscibility Boundaries of the Systems K2O—SiO2, K2O—Li2O—SiO2, K2O—Na2O—SiO2, and K2O—BaO—SiO2", Journal of the American Ceramic Society, vol. 64, No. 5 (May 1981) pp. 289-292.
(Continued)

*Primary Examiner* — Charlie Y Peng
(74) *Attorney, Agent, or Firm* — Millen, White, Zelano, Branigan, P.C.

(57) ABSTRACT

The invention relates to an optical scattering element suitable for dispersing or scattering light transmitted by optical device by Mie scattering. The optical scattering element comprises a phase-separated or porous borosilicate glass having dispersed phase particles with a particle size of 200 to 500 nanometers or pores with a size of 200 to 500 nanometers, at a number density of $10^8$ to $10^{12}$ mm$^{-3}$. The optical scattering element can be prepared by subjecting a borosilicate glass to a controlled heat treatment to induce phase separation, and then optionally leaching out one of the phases with an acid leach. The optical scattering element can be, for example, attached to an end of an optical fiber or bundle of optical fibers. The invention also relates to a method of dispersing or scattering light by transmitting the light through the optical scattering element.

36 Claims, 2 Drawing Sheets

(51) Int. Cl.
*F21V 8/00* (2006.01)
*C03C 3/089* (2006.01)
*C03C 3/093* (2006.01)
*C03C 11/00* (2006.01)
*C03C 13/04* (2006.01)
*G02B 6/24* (2006.01)

(52) U.S. Cl.
CPC .......... *C03C 11/005* (2013.01); *C03C 13/046* (2013.01); *G02B 6/0008* (2013.01); *G02B 6/0016* (2013.01); *C03C 2204/04* (2013.01); *G02B 6/241* (2013.01)

(56) References Cited

U.S. PATENT DOCUMENTS

| | | | |
|---|---|---|---|
| 3,650,721 A | | 3/1972 | Hammel et al. |
| 3,758,284 A | | 9/1973 | Haller |
| 5,250,095 A | | 10/1993 | Sigel |
| 2002/0094161 A1 | | 7/2002 | Maitland |
| 2002/0186921 A1* | | 12/2002 | Schumacher et al. .......... 385/31 |
| 2005/0163422 A1* | | 7/2005 | Iwasaki ........................ 385/24 |
| 2009/0262428 A1* | | 10/2009 | Kurokawa ........... G02B 5/0215 359/599 |
| 2011/0103757 A1* | | 5/2011 | Alkemper et al. ........... 385/124 |
| 2013/0017387 A1 | | 1/2013 | James, III et al. |

OTHER PUBLICATIONS

W.A. Zdaniewski, "Microstructure and Kinetics of Crystallization of MgO—Al2O3—SiO2 Glass-Ceramics", Journal of the American Ceramic Society, vol. 61, No. 5-6 (May-Jun. 1978) pp. 199-204.

M.S. Randall et al., "Primary and Secondary Phase Separation in CdF2—LiF—AlF3—PbF2 Glasses", Journal of the American Ceramic Society, vol. 71, No. 12 (1988) pp. 1134-1141.

M.L. Huggins et al., "Calculation of Density and Optical Constants of a Glass From Its Composition in Weight Percentage", Journal of the American Ceramic Society, vol. 26, No. 1 (1943) pp. 4-11.

C.F. Bohren et al., "Absorption and Scattering of Light by Small Particles", A Wiley Interscience Publication—John Wiley & Sons (1983) pp. 82-129.

A.J. Cox et al., "An Experiment to Measure Mie and Rayleigh Total Scattering Cross Sections", American Journal of Physics, vol. 70, No. 6 (Jun. 2002) pp. 620-625.

PCT International Search Report mailed Jul. 15, 2014 in corresponding International Application No. PCT/US2014/024241. (3 pages).

PCT Written Opinion of the International Searching Authority dated Jul. 15, 2014 in corresponding International Application No. PCT/US2014/024241. (3 pages).

\* cited by examiner

Fig. 2

| OPTICAL FIBER | OPTICAL ELEMENT |
| OPTICAL FIBER | OPTICAL ELEMENT |

Fig. 3

| OPTICAL FIBER | OPTICAL |
| OPTICAL FIBER | ELEMENT |

OPTICAL ELEMENT FOR MIE SCATTERING LIGHT FROM AN OPTICAL FIBER

SUMMARY OF THE INVENTION

The invention relates to adjusting Mie scattering of visible light transmitted from an optical fiber. In particular, the invention relates to an optical element that can be affixed to the end of an optical fiber that will scatter light predominantly in the forward direction, a method of manufacturing such an optical element, and the use of such an optical element in the fields of illumination, sensors and medical devices.

Electromagnetic radiation passing through a medium, such as an optical fiber, will be scattered by interactions with defects/inhomogeneities in the medium, that is a volume of variant refractive index, such as a particle, bubble, droplet, or even a density fluctuation. When the defect/inhomogeneity is less than one-tenth of the operating wavelength of light, the scattering is referred to as Rayleigh scattering, named after Lord Rayleigh (John Strutt). For example, the blue color of the sky is caused by Rayleigh scattering as a result of gas molecules in the atmosphere. When the defect/inhomogeneity is comparable in size to the wavelength, i.e., larger than 10% of wavelength, the scattering is known as Mie scattering, named after German physicist Gustav Mie. Thus, for example, the scattering of light induced by aerosols and pollutants in the atmosphere is Mie scattering. The white appearance of clouds is a result of Mie scattering. Rayleigh scattering and Mie scattering are both forms of elastic light scattering, that is the energy (and thus wavelength and frequency) of the light is not substantially changed by the interaction with the scattering particle.

The amount of scattered radiation and the directions in which the radiation is scattered as a result of Mie scattering are dependent on the size and composition of the particle (feature), as well as the wavelength of the radiation and the refractive index of the medium.

Particles that have a size which is applicable for inducing Mie scattering will scatter the radiation in a predictable way. In general, the radiation is scattered all around the particle. While more of the radiation is scattered on the side of the particle facing away from the source of the radiation, some amount of radiation will be scattered back in the direction of the source of the radiation.

The type of scattering considered herein, Mie scattering, makes use of relatively large features (hundreds of nanometers) to induce scattering efficiently in the forward direction. This is useful to increase the spread from an optic for illumination purposes (i.e., to thereby illuminate a larger area) while maintaining efficiency (i.e., efficient transmission).

For example, in accordance with the invention, to scatter light emanating from the end of an optical fiber, one can attach an optical element that will induce Mie scattering. In this regard, it is desirable that the optical element be designed to optimize scattering in the forward direction. Therefore, one aspect of the present invention is to provide an optical element (scattering element or scattering optic) for inducing Mie scattering of visible light from an optical fiber, where the element is comprised of nanoscale features that will scatter light predominantly in the forward direction when affixed to the end of an optical fiber such as a high silica fiber.

Therefore, in accordance with the invention, there is provided an optical element made of porous or phase-separated glass which is designed to optimize scattering in the forward direction (i.e. increased scattering cross-section in this direction) and minimize scatter in the backward direction, while at the same time attaining the desired solid angle of scattered light in the forward direction (in other words, maintaining good spread out of the optical fiber).

While the optical element of the invention is generally described for use with an optical fiber, the element can be used in any optics applications for dispersing or scattering light transmitted by an optical device. Therefore, in accordance with another aspect of the invention, there is provided a method for dispersing or scattering light transmitted by an optical device by transmitting the light through an optical element made of porous or phase-separated glass which is designed to optimize scattering in the forward direction (i.e. increased scattering cross-section in this direction) and minimize scatter in the backward direction, while at the same time maintaining good spread.

Thus, according to one aspect of the invention there is provided a scattering optical element produced by subjecting a glass composition, formed from a glass system that undergoes phase separation (for example, the classic borosilicate glass system; the systems $K_2O$—$SiO_2$, $K_2O$—$Li_2O$—$SiO_2$, $K_2O$—$Na_2O$—$SiO_2$, and $K_2O$—$BaO$—$SiO_2$ (Kawamoto and Tomozawa, 1981, J. Amer. Ceram. Soc., vol. 64 (5), 289-292); the system $MgO$—$Al_2O_3$—$SiO_2$ (Zdaniewski, 1978, J. Amer. Ceram. Soc., vol. 61 (5-6), p. 199-204); and the system $CdF_2$—$LiF$—$AlF_3$—$PbF_2$ (Randall et al., 1988, J. Amer. Ceram. Soc., vol. 71 (12), p. 1134-1141) to a phase separation process, such as by means of a controlled thermal treatment, whereby the glass composition separates into two phases, and optionally a further procedure for creating open porosity within the glass by a leach step to obtain a glass having pores on the order of 200 to 500 nanometers, preferably 300-500 nm, especially 300-450 nm with a number density approaching $10^8$ to $10^{12}$ $mm^{-3}$, preferably $10^9$ to $10^{11}$ $mm^{-3}$, especially preferably $10^{10}$ to $10^{11}$ $mm^{-3}$.

According to one aspect of the invention there is provided a scattering optical element produced by melting a borosilicate glass (preferably an alkali borosilicate glass) that, after being annealed, is subjected to phase separation using a well-controlled thermal treatment whereby the composition separates into a silica-rich phase and a boron-rich phase, and optionally a further procedure for creating open porosity within the glass by an acid leach step and a pore cleaning caustic leach step, to obtain a glass having pores on the order of 200 to 500 nanometers, preferably 300-500 nm, especially 300-450 nm with a number density approaching $10^8$ to $10^{12}$ $mm^{-3}$, preferably $10^9$ to $10^{11}$ $mm^{-3}$, especially preferably $10^{10}$ to $10^{11}$ $mm^{-3}$.

According to one aspect of the invention there is provided a device comprising at least one optical fiber and at least one Mie scattering optical element for dispersing light emitted from the at least one optical fiber, wherein the at least one Mie scattering optical element comprises a phase-separated or porous glass (such as a borosilicate glass, preferably an alkali borosilicate glass) having dispersed phase particles with a particle size of 200 to 500 nanometers or pores having a size of 200 to 500 nanometers, at a number density of $10^8$ to $10^{12}$ $mm^{-3}$.

According to another aspect of the invention there is provided an endoscope comprising an optical fiber or optical fiber bundle and an optical scattering element attached to the distal end of said optical fiber or optical fiber bundle for dispersing light emitted from the distal end of the optical fiber or optical fiber bundle, the optical scattering element comprising a phase-separated or porous glass (such as a borosilicate glass, preferably an alkali borosilicate glass) having dispersed phase particles with a particle size of 200 to 500 nanometers or pores having a size of 200 to 500 nanometers, at a number density of $10^8$ to $10^{12}$ mm$^{-3}$.

According to another aspect of the invention there is provided a process for preparing an optical device with a Mie scattering optical element, the process comprising: preparing a Mie scattering optical element by subjecting an annealed glass (such as a borosilicate glass, preferably an alkali borosilicate glass) to a phase separation using a controlled thermal treatment, and optionally subjecting the phase-separated glass to an acid leach to create pores and a caustic leach to clean the resultant pores, and attaching the resultant Mie scattering optical element to the end of an optical fiber or to the end of a bundle of optical fibers.

According to a further aspect, there is provided a method for dispersing or scattering light transmitted by optical device by transmitting the light through an optical scattering element comprising a phase-separated or porous glass (for example, a borosilicate glass or an alkali borosilicate glass) having dispersed phase particles with a particle size of 200 to 500 nanometers or pores having a size of 200 to 500 nanometers, at a number density of $10^8$ to $10^{12}$ mm$^{-3}$.

For example, the optical scattering element can be prepared by melting a borosilicate glass, preferably an alkali borosilicate glass, that, after being annealed, is subjected to a phase separation using a well-controlled thermal treatment, and optionally a further procedure for creating open porosity within the glass by an acid leach step and a pore cleaning caustic leach step, to obtain a glass having pores on the order of 200 to 500 nanometers, preferably 300-500 nm, especially 300-450 nm with a number density approaching $10^8$ to $10^{12}$ mm$^{-3}$, preferably $10^9$ to $10^{11}$ mm$^{-3}$, especially preferably $10^{10}$ to $10^{11}$ mm$^{-3}$.

Based on standard Mie scattering calculations, it is believed that the Mie scattering required to optimize scattering in the forward direction while maintaining good spread out of a fiber, and minimal scatter in the backward direction, can be attained with features (scattering centers) on the order of 200-500 nm diameter at an approximate number density of $10^8$ to $10^{12}$ mm$^{-3}$, and with an approximately equal volume fraction for each phase, e.g., a silica rich phase and a boron rich phase.

In accordance with the invention, thermal treatment of the mother borosilicate glass, preferably alkali borosilicate glass (see, for example, the compositions listed in Table 1), induces glass-in-glass phase separation. The phases are defined as a silica rich phase and a boron rich phase. After undergoing the heat treatment, the mother glass can then be chemically leached. When the mother glass is chemically leached the host or bulk phase is considered to be the silica rich phase, and the pores resulting from the removal of the boron rich phase is considered the scattering feature.

This combination of feature size and number density can achieve a scattering cross section of $10^{-4}$ to $10^{-2}$ μm$^{-2}$, preferably $5\times10^{-3}$ to $5\times10^{-2}$ μm$^2$. For this set of conditions, the amount of light scattered in the backward direction is less than 1% of that scattered in the forward direction.

In order to obtain a glass exhibiting such a combination of nanoscale features on the order of 200-500 nm with a number density approaching $10^8$ to $10^{12}$ mm$^{-3}$, the glass should be subjected to a well-controlled thermal processing profile. For example, in terms of commercially available products, SCHOTT CoralPor™ Porous Glass is a glass product which has applications in chromatography media, reference electrode junctions, host material for sensors, and as an additive (filler) in coatings (see James et al., US 2013/0017387). During manufacture, CoralPor™ Porous Glass is subjected to a carefully controlled thermal treatment to induce glass-in-glass phase separation. This heat treatment ultimately dictates the final size of the scattering features present in the material. As a result, the manufacturing process can be manipulated to produce CoralPor™ Porous Glass in a form which satisfies the desired criteria, i.e., 200-500 nm features at a number density of $10^8$ to $10^{12}$ mm$^{-3}$.

Processes are known for the manufacturing of porous glass by phase separation. Hood et al. (U.S. Pat. No. 2,106,744) disclose a process wherein a borosilicate glass is subjected to a thermal treatment in order to induce separation of two phases, one phase rich in silica (the insoluble phase) and the other rich in alkali and boron oxide (the soluble phase). In the process, the metal oxides are melted in a furnace and then subjected to a heat treatment (e.g., 525° C. for three days) which causes the glass to separate into the two phases which is characterized by the glass obtaining bluish opalescence, which indicates Rayleigh scattering rather than Mie scattering. Thereafter, the heat treated glass is immersed in an acid bath to leach out the soluble phase.

Haller et al. (U.S. Pat. No. 3,549,524; U.S. Pat. No. 3,758,284) describe porous separation materials for use in separating components of a liquid mixture by chromatography. To manufacture the separation materials, a base borosilicate glass is subjected to a heat treatment to separate two phases, a silica-rich phase and a boron-rich phase. The heat treated glass is then treated with acid to leach out the boron-rich phase. Haller et al. disclose that the one can achieve the desired pore size and narrow distribution thereof through the specific heat treatment and that the dependence of pore size and distribution are expressed by the following equation: $r^n = kte^{-m/T}$, wherein r is pore radius, k, m and n are constants, T is heat treatment (in Kelvin), and t is time (in hours). The heat treatment can be at a temperature of 400-950° C. for a time period of 2 hours to 4 weeks.

Hammel et al. (U.S. Pat. No. 3,650,721) describe a process for forming a microporous borosilicate glass suitable for filtering tobacco smoke. The glass is prepared by melting the glass composition and then heat treating the glass at a temperature of about 450° C. to about 750° C. for a time period of 1 hour or more. Hammel et al. discloses that heat treating at higher temperatures for longer time periods causes the borate-rich phase to agglomerate, thereby resulting in the formation of larger pores during the leaching step.

In accordance with the invention, the scattering optical elements can be produced by, for example, melting a borosilicate glass, preferably alkali borosilicate glass that, after being annealed, is subjected to a phase separation using a well-controlled thermal treatment in the temperature range of 500-800° C., such as 600-800° C., preferably 650-750° C., more preferably 700-725° C., for a time period of, for example, 1 to 150 hours, such as 24 to 48 hours or 48 to 80 hours. For example, for a given composition, the thermal treatment employed to achieve nanoscale features of approximately 200 nanometers may involve a duration of 20-26 hours at 700° C.

The conditions can be adjusted based on the melt parameters used (i.e., temperature and quenching method) and composition. In general, the process employed is dependent on desired phase growth. For example, within the phase separation region, generally, increased temperature for longer durations leads to larger feature size, although the size of the features will also depend on the specific composition.

This thermal treatment processing can be considered complete for some applications. In other words, for some applications, no further processing steps are required to achieve the desired results of 200-500 nm features with a number density approaching $10^8$ to $10^{12}$ mm$^{-3}$.

However, the process can also include a further procedure for creating open porosity within the glass. This open porosity can be obtained by employing conventional chemical leaching protocols comprising the use of a pore forming (i.e., open porosity) acid leach and a pore cleaning caustic leach. In final, glasses exposed to the entire process (phase separation and chemical leaching) reveal pore sizes, as measured by mercury intrusion porosimetry, on the order of 200 to 500 nanometers with a number density approaching $10^8$ to $10^{12}$ mm$^{-3}$.

Suitable acids and caustic materials for the acid leach and pore cleaning caustic leach are described in U.S. Pat. No. 2,106,744, U.S. Pat. No. 3,549,524; U.S. Pat. No. 3,758,284, and U.S. Pat. No. 3,650,721, cited above. Thus, for example, suitable acids include inorganic acids such as hydrochloric acid, sulfuric acid, and nitric acid, and suitable caustic materials include alkali metal hydroxides such as sodium hydroxide or potassium hydroxide.

The base glass can be, for example, any borosilicate glass that has suitable silica and borate contents for phase separation to occur and a sufficient borate content to achieve the desired number density of nanoscale features. Preferably, the borosilicate glass contains at least some alkali metal oxide. For example, in accordance with an embodiment of the invention, the base glass composition comprises (based on wt. %):

| | |
|---|---|
| $B_2O_3$ | 15.00-40.00 |
| $SiO_2$ | 45.00-80.00 |
| $R_2O$ | 0.0-20.0 |
| R'O | 0.0-20.00 |
| R"$O_2$ | 0.0-10.00 |
| $Al_2O_3$ | 0.0-10.00 | wherein $R_2O$ is the sum of $Li_2O$, $Na_2O$, $K_2O$, $Rb_2O$, and $Cs_2O$ (and is preferably greater than 0), R'O is the sum of BaO, CaO, MgO, SrO, PbO, and ZnO, and R"$O_2$ is the sum of $TiO_2$, $ZrO_2$, and $HfO_2$.

With regards to ranges described herein, all ranges include at least the two endpoints of the ranges, as well as all values between the two endpoints. Thus, for example, a range of 1 to 10 is to be understood as expressly disclosing at least the values of 1.0, 1.5, 2.0, 2.8, 3.0, 3.1, 4.0, 4.2, 5.0, 5.3, 6.0, 7.0, 7.7 8.0, 9.0, 9.9 and 10.0.

In the borosilicate base glass, $SiO_2$ functions as a primary network former. Thus, according to another aspect of the invention, the borosilicate base glass composition contains 45.00-80.00 wt. % of $SiO_2$, for example, 45.00-75.00 wt. % of $SiO_2$, or 45.00-70.00 wt. % of $SiO_2$, or 45.00-65.00 wt. % of $SiO_2$, or 45.00-60.00 wt. % of $SiO_2$, or 50.00-60.00 wt. % of $SiO_2$.

In the borosilicate base glass, $B_2O_3$ functions as a network former and as primary former of the nanoscale features of the resultant phase separated/porous glass. Thus, according to another aspect of the invention, the borosilicate base glass composition contains 15.00-40.00 wt. % of $B_2O_3$, for example, 20.00-35.00 wt. % of $B_2O_3$, or 20.00-30.00 wt. % of $B_2O_3$.

According to another aspect, the borosilicate base glass composition contains 0.00-20.00 wt. % of $R_2O$ (preferably >0.00-20.00 wt. % of $R_{2O}$), wherein $R_2O$ is the sum of $Li_2O$, $Na_2O$, $K_2O$, $Rb_2O$, and $Cs_2O$) for example, 1.00-15.00 wt. % $R_{2O}$, or 1.00-10.00 wt. % $R_{2O}$, or 2.00-8.00 wt. % $R_{2O}$.

According to another aspect, the borosilicate base glass composition contains 0.00-20.00 wt. % of R'O (sum of BaO, CaO, MgO, SrO, PbO, and ZnO) for example, 1.00-15.00 wt. % R'O, or 1.00-10.00 wt. % R'O, or 2.00-8.00 wt. % R'O. The R'O metal oxides can be used to adjust the refractive index of each phase.

According to another aspect, the borosilicate base glass composition contains 0.00-10.00 wt. % of R"$O_2$ (sum of $TiO_2$, $ZrO_2$, and $HfO_2$) for example, 0.00-8.00 wt. % R"$O_2$, or 1.00-8.00 wt. % R"$O_2$, or 0.00-5.00 wt. % R"$O_2$, or 1.00-5.00 wt. % R"$O_2$. These metal oxides can be used to enhance chemical durability, and can be used to adjust the refractive index of each phase.

In the borosilicate base glass composition, $Al_2O_3$ generally acts as a network co-former and can also be used to enhance chemical durability. Thus, according to another aspect, the borosilicate base glass composition according to the invention contains 0.00-10.00 wt. % of $Al_2O_3$, for example, 0.00-8.00 wt. % of $Al_2O_3$, or 1.00-8.00 wt. % of $Al_2O_3$, or 0.00-5.00 wt. % of $Al_2O_3$, or 1.00-5.00 wt. % of $Al_2O_3$, or 2.50-5.00 wt. % of $Al_2O_3$.

According to a further aspect, the base glass can be a glass in accordance with glass composition described in James et al. US 2013/0017387. This glass composition comprises (based on wt. %): 40-80% $SiO_2$, 5-35% $B_2O_3$ and 1-10% $Na_2O$, preferably 45-65% $SiO_2$, 20-30% $B_2O_3$ and 2-8% $Na_2O$, and more preferably 50-55% $SiO_2$, 25-27% $B_2O_3$ and 5-7% $Na_2O$. As disclosed in US 2013/0017387 the glass can include other ingredients such as, for example, $ZrO_2$, $TiO_2$, $Al_2O_3$, CaO and/or ZnO, and optionally further ingredients, e.g., oxides of Mg, Fe, Mn, Ce, Sn, etc.

The optical element according to the invention can be affixed to an optical fiber or optical fiber bundle via any suitable process such as fusion splicing, optical contacting via precision polishing, silicone adhesive, organic adhesive, or reactive nanofoil (such as that purchased from Indium Corporation of America).

In order to affix the scattering element to an optical fiber or optical fiber bundle, the output surface of the light guide (single fiber or fiber bundle) and the input surface of the scattering optic or scattering element must be prepared (e.g., cleaned and cleaved). After the surfaces are prepared, the format (e.g., size, geometry) of the optics to be joined is considered, and the method of adhesion is selected. In one example, a scattering element is affixed to a single optical fiber using a commercially available fusion splicing instrument, where arc fusion is employed to create an optical joint. In a second example an optically clear silicone adhesive is applied to the surface of a fiber bundle and the scattering element is adhered to the surface via the silicone adhesive. A third example employs a flange of nanofoil which when activated (for example, by applying a potential across the foil) produces high temperature in a localized area to join the fiber to the scattering optic.

For example, the optical element according to the invention can be used in in conjunction with a single optical fiber or a bundle of optical fibers that forms part of an endoscope. Thus, in accordance with a further aspect, the invention relates to an endoscope comprising an optical fiber or optical fiber bundle wherein at the distal end of the optical fiber or optical fiber bundle (the end away from the user) there is a provided an optical scattering element for dispersing light emitted from the distal end of the optical fiber or optical fiber bundle, the optical scattering element comprising a phase-separated or porous borosilicate glass having dispersed phase particles with a particle size of 200 to 500 nanometers or pores having a size of 200 to 500 nanometers, at a number density of $10^8$ to $10^{12}$ mm$^{-3}$.

BRIEF DESCRIPTION OF THE DRAWINGS

The invention and further details, such as features and attendant advantages, of the invention are explained in more detail below on the basis of the exemplary embodiments which are diagrammatically depicted in the drawings, and wherein:

FIG. 2 shows an embodiment wherein several optical fibers are each provided with a Mie scattering element attached to an end thereof; and FIG. 3 shows an embodiment wherein a single Mie scattering element is attached to the ends of a plurality of optical fibers.

EXAMPLES

Figure 1:
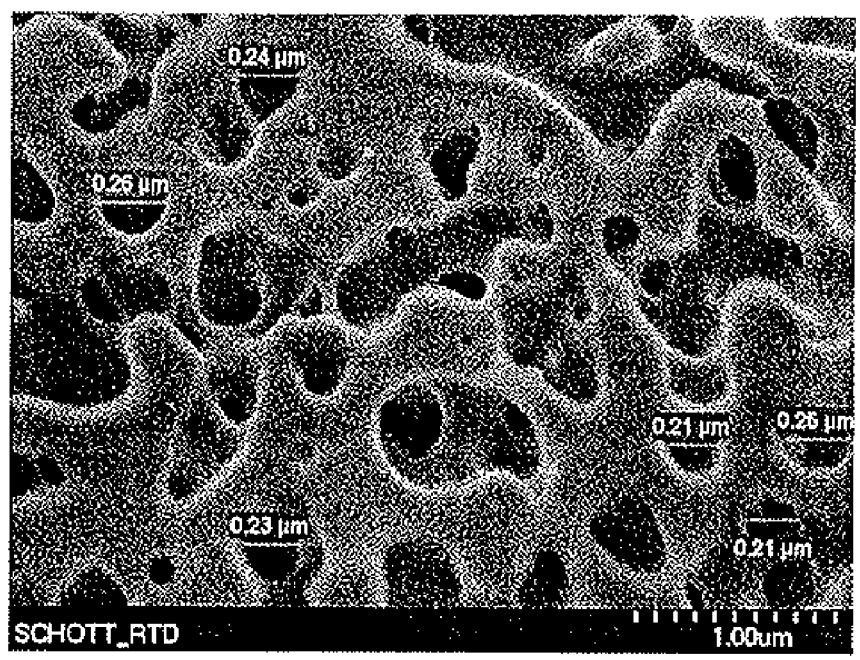
FIG. 1 shows a scanning electron microscope image of a porous glass derived from composition A of Table 1.

The base glasses can be made by combining the components in their metal oxide forms and melting the resultant mixture with the help of stirring using a platinum stirrer for better homogeneity. The glasses can then be cast into moulds and appropriately annealed in order to remove the stress as the liquid cools to the amorphous state. The resulting glass slabs can then be shaped into forms required for use with the instruments that measure the various properties of the glasses, drawn to fiber, or machined to numerous geometries for joining to optical fiber or optical fiber bundles.

The following Tables 1A-1D present examples of suitable base glasses for use in with invention.

TABLE 1A

Glass compositions on an oxide-weight percent basis

| Oxide | A | B | C | D | E | F |
|---|---|---|---|---|---|---|
| SiO$_2$ | 52.40 | 52.77 | 50.93 | 56.85 | 54.85 | 56.85 |
| B$_2$O$_3$ | 25.99 | 25.87 | 25.73 | 30.31 | 30.31 | 30.31 |
| Al$_2$O$_3$ | 3.42 | 3.41 | 3.39 | | | |
| Na$_2$O | 5.92 | 5.89 | 5.86 | 6.90 | 6.90 | 6.90 |
| CaO | 5.14 | 5.12 | 5.09 | | | |
| ZnO | | | | 3.00 | 4.00 | 2.00 |
| TiO$_2$ | 2.00 | | 2.00 | | | 2.00 |
| ZrO$_2$ | 5.14 | 6.94 | 7.00 | 3.00 | 4.00 | 2.00 |

TABLE 1B

Glass compositions on an oxide-weight percent basis

| Oxide | G | H | I | J | K | L |
|---|---|---|---|---|---|---|
| SiO$_2$ | 54.85 | 58.92 | 57.68 | 58.69 | 57.69 | 60.19 |
| B$_2$O$_3$ | 30.31 | 28.41 | 27.81 | 28.30 | 27.82 | 29.02 |
| Al$_2$O$_3$ | | | | | | |
| Na$_2$O | 6.90 | 6.47 | 6.33 | 6.44 | 6.33 | 6.61 |
| CaO | | | | | | |
| ZnO | 3.00 | 3.10 | 4.09 | 2.06 | 3.05 | 2.10 |
| TiO$_2$ | 2.00 | | | 1.33 | 1.97 | |
| ZrO$_2$ | 3.00 | 3.09 | 4.09 | 3.18 | 3.14 | 2.80 |

TABLE 1C

Glass compositions on an oxide-weight percent basis

| Oxide | M | N | O | P | Q | R |
|---|---|---|---|---|---|---|
| SiO$_2$ | 56.86 | 57.47 | 53.28 | 50.61 | 52.70 | 52.12 |
| B$_2$O$_3$ | 27.43 | 27.72 | 26.43 | 26.23 | 26.14 | 25.86 |
| Al$_2$O$_3$ | | | | | | |
| Na$_2$O | 6.24 | 6.31 | 6.02 | 5.97 | 5.95 | 5.89 |
| CaO | | | | | | |
| ZnO | 5.41 | 5.49 | 5.23 | 5.20 | 5.18 | 5.12 |
| TiO$_2$ | | | 2.00 | 6.98 | 2.00 | 2.01 |
| ZrO$_2$ | 4.03 | 3.01 | 7.03 | 5.00 | 8.02 | 8.99 |

TABLE 1D

Glass compositions on an oxide-weight percent basis

| Oxide | S | T |
|---|---|---|
| SiO$_2$ | 60.19 | 54.15 |
| B$_2$O$_3$ | 29.02 | 26.11 |
| Al$_2$O$_3$ | | 3.45 |
| Na$_2$O | 6.61 | 5.68 |
| CaO | | |
| ZnO | 2.10 | 5.17 |
| TiO$_2$ | | |
| ZrO$_2$ | 2.08 | 5.18 |

Example 1

Glass-in-glass phase separation is employed to create in the glass features on the order of 250 nm to induce Mie scattering primarily in the forward direction. A base glass of composition A from Table 1 is exposed to a carefully controlled heat treatment wherein the base glass is subjected to a soak temperature of 700° C. for 24 hours. The resultant glass is opaque and white in color.

To support the proposed Mie scattering behavior of the phase separated glass in the visible region of the electromagnetic spectrum (400-800 nm), Mie scattering calculations were performed using the approach outlined in Bohren and Huffman (*Absorption and Scattering of Light by Small Particles*, Wiley-VCH, 1983, pp. 82-89). Assuming a typical observation wavelength of 550 nm, 300-nm feature sizes and 50% volume proportions of the two phases as actually observed in the phase-separated samples, calculated refractive indices for the two glassy phases (1.53 and 1.46) based on the model of Huggins and Sun (J. Amer. Ceram. Soc., vol. 26, p 4-11, 1943) with compositions estimated from mass-balance consideration of the phase-separated glass, calculations reveal a feature number density of $3.5 \times 10^{13}$ mm$^{-3}$, a scattering cross-section of $1.5 \times 10^{-3}$ μm$^2$, and a scattering coefficient of 523 cm$^{-1}$. Further, for this particular parameter set, the forward scatter component is over 100 times stronger than the back-scatter component, a desirable feature to increase the efficiency of the out-coupled light and to reduce the thermal load of the fiber. Note that this scenario (550 nm, 300-nm feature sizes, 50% volume proportions of the two phases, and the calculated refractive indices) is meant solely as an example of what can be attained using phase-separated glass.

Example 2

A plate of composition A from Table 1 is fabricated and exposed to the same phase separation heat treatment as described in Example 1. The phase separated sample is then exposed to a chemical leaching process comprised of an acid wash (e.g., 10% hydrochloric acid, 95° C.) to create open porosity and a basic wash (e.g., 0.5 N sodium hydroxide, room temperature) to remove any residual material in the porous matrix. The product of this process is a porous glass that exhibits pores on the order of 250 nm (FIG. 2).

In this example, the Mie scattering is the result of the size of the nanoscale features that yield the open porosity, i.e., the pores (average pore size approximately 250 nm), and the difference in refractive index between the silica matrix and the air filled pores. Assuming the same set of conditions as in Example 1, but now with refractive indices of 1.50 and 1.00 (for the voids), the calculated Mie scattering turbidity coefficient is around 2000 $mm^{-1}$ at 400 nm wavelength and 850 $mm^{-1}$ at 800 nm, much higher than the glass of Example 1 due to the larger refractive index differential.

Following the examples listed above one skilled in the art can produce scattering optical elements in a variety of formats. For example, from melt, the original glass can be cast into plates, discs, other irregular geometries, or drawn to an optical fiber.

Furthermore, glass compositions such as those found in Table I can be drawn to form an optical fiber using well-known, accepted industrial processes. Here, a single-fiber can be employed, where a porous fiber can be partially exposed to a pore closing heat treatment as taught by Hood and Nordberg (U.S. Pat. No. 2,106,744) to produce a high silica fiber with a porous end that act as the scattering optical element as described in Example 2. Thus, according to a further aspect of the invention there is provided a process of preparing an optical device comprising an optical fiber and a Mie scattering optical element, the process comprising preparing a porous glass, formed from a glass system that undergoes phase separation (for example, a borosilicate glass, preferably an alkali borosilicate glass), drawing the glass into a porous fiber and subjecting the drawn porous glass to a pore closing heat treatment to produce an optical fiber with a porous end, the porous end being a Mie scattering optical element having pores having a size of 200 to 500 nanometers, at a number density of $10^8$ to $10^{12}$ $mm^{-3}$.

Additionally, a single fiber produced from glass compositions such as those found in Table 1 can be exposed to a thermal treatment to induce glass-in-glass phase separation. The phase separated fiber can then be partially chemically leached such that the end of the fiber remains phase separated (e.g., non-porous). The pores created by the chemical leaching procedure can then be closed with a pore closing thermal treatment such as that taught by Hood and Nordberg (U.S. Pat. No. 2,106,744). Here, the entire fiber is non-porous, and comprised of two regions—a high silica, non-scattering region and a phase separated Mie scattering region. Thus, according to another aspect of the invention there is provided a process of preparing an optical device comprising an optical fiber and a Mie scattering optical element, the process comprising preparing a glass, formed from a glass system that undergoes phase separation (for example, a borosilicate glass, preferably an alkali borosilicate glass), drawing the glass into a fiber, subjecting the fiber to controlled thermal treatment to induce phase separation, partially subjecting the phase-separated fiber to an acid leach to create pores to form a fiber having a porous region and a non-porous end, and subject the porous region of the fiber to a pore closing heat treatment to produce an optical fiber with a phase-separated non-porous end, the non-porous end being a Mie scattering optical element having dispersed phase particles with a particle size of 200 to 500 nanometers, at a number density of $10^8$ to $10^{12}$ $mm^{-3}$.

Furthermore, glass compositions such as those found in Table 1 can be drawn to an optical fiber. The resultant optical fiber can be partially inserted into a furnace to be heat treated only at one end. Here, a single optical fiber is produced that is capable of Mie scattering light. Thus, according to a further aspect of the invention there is provided a process of preparing an optical device comprising an optical fiber and a Mie scattering optical element, the process comprising preparing a glass, formed from a glass system that undergoes phase separation (for example, a borosilicate glass, preferably an alkali borosilicate glass), drawing the glass into a fiber, subjecting one end of the fiber to controlled thermal treatment to induce phase separation in that end of the fiber, and optionally subjecting the phase-separated fiber end to an acid leach to create pores and a caustic leach to clean the resultant pores, to convert the treated end of the fiber to a Mie scattering optical element having dispersed phase particles with a particle size of 200 to 500 nanometers or pores having a size of 200 to 500 nanometers, at a number density of $10^8$ to $10^{12}$ $mm^{-3}$.

Alternatively, rather than heating the fiber end in a furnace, the end of the single optical fiber can be irradiate with a high power laser to induce glass in glass phase separation.

In order to close the pores of a porous glass, the glass is exposed to a multistep thermal treatment. Initially, the porous glass is held at a low temperature (~200° C.) to vaporize water contained within the glass. Next, the temperature is slowly increased to consolidate the open porosity (i.e., sinter) to create a non-porous glass. Here, temperatures exceeding 1000° C. are employed.

The scattering optical elements comprised of phase separated glass or porous glass, in accordance with the invention, have commercial value in the general field of illumination, optical devices and sensors. For example, affixing the scattering optical element of the present invention to an optical fiber, can be employed in medical devices, such as optical fibers for use in ocular surgery. Two specific advantages of the inventive scattering optical elements in the fields of optical devices and sensors are the tunability of the scattering features over a range of sizes (i.e., 200-500 nm) by varying the heat treatment/leaching conditions and the ability to fabricate the glass products in a variety of formats (e.g., plate, fiber, etc.).

The entire disclosure[s] of all applications, patents and publications, cited herein, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device comprising one or more optical fibers and one or more Mie scattering optical elements for dispersing light, emitted from said at least one optical fiber, predominantly in the forward direction, wherein at least one of said one or more optical fibers has one of said one or more Mie scattering elements attached to an end thereof, and wherein said one or more Mie scattering optical elements each comprise a phase-separated glass having dispersed phase particles with a particle size of 200 to 500 nanometers or a porous glass having pores with a size of 200 to 500 nanometers, at a number density of $10^8$ to $10^{12}$ $mm^{-3}$.

2. A device according to claim 1, wherein said phase-separated glass or porous glass is a phase-separated or porous borosilicate glass.

3. A device according to claim 1, wherein said phase-separated glass or porous glass is a phase-separated or porous alkali borosilicate glass.

4. The device according to claim 1, wherein said one or more Mie scattering optical elements each comprise a phase-separated borosilicate glass wherein the particles of the dispersed phase have particle size of 200 to 500 nanometers at a number density of $10^8$ to $10^{12}$ mm$^{-3}$.

5. The device according to claim 4, wherein said one or more Mie scattering optical elements each comprise an alkali phase-separated borosilicate glass wherein the particles of the dispersed phase have particle size of 200 to 500 nanometers at a number density of $10^8$ to $10^{12}$ mm$^{-3}$.

6. The device according to claim 1, wherein said at one or more Mie scattering optical elements each comprise a porous borosilicate glass wherein glass have pores with a pore size of 200 to 500 nanometers at a number density of $10^8$ to $10^{12}$ mm$^{-3}$.

7. The device according to claim 6, wherein said one or more Mie scattering optical elements each comprise an alkali porous borosilicate glass wherein glass have pores with a pore size of 200 to 500 nanometers at a number density of $10^8$ to $10^{12}$ mm$^{-3}$.

8. The device according to claim 4, wherein said particles of the dispersed phase have particle size of 300 to 500 nanometers.

9. The device according to claim 4, wherein said particles of the dispersed phase have particle size of 300 to 450 nanometers.

10. The device according to claim 6, wherein said pores have a pore size of 300 to 500 nanometers.

11. The device according to claim 6, wherein said pores have a pore size of 300 to 450 nanometers.

12. The device according to claim 1, wherein said dispersed phase particles or said pores have a number density of $10^9$ to $10^{11}$ mm$^{-3}$.

13. The device according to claim 12, wherein said dispersed phase particles or said pores have a number density of $10^{10}$ to $10^{11}$ mm$^{-3}$.

14. The device according to claim 1, wherein said device is capable of providing a scattering cross section of $10^4$ to $10^{-2}$ μm$^2$ for light emitted though said at least one Mie scattering optical element.

15. The device according to claim 14, wherein said device is capable of providing a scattering cross section of $5 \times 10^{-3}$ to $5 \times 10^{-2}$ μm$^2$.

16. The device according to claim 2, wherein said one or more Mie scattering optical elements are prepared by subjecting an annealed borosilicate glass to a phase separation using a controlled thermal treatment, and optionally subjecting the phase-separated borosilicate glass to an acid leach to create pores and a caustic leach to clean the resultant pores.

17. The device according to claim 16, wherein said controlled thermal treatment comprising heating the annealed borosilicate glass at a temperature of 500-800° C. for a time period of 1 to 150 hours.

18. The device according to claim 16, wherein said controlled thermal treatment comprising heating the annealed borosilicate glass at a temperature of 600-800° C. for a time period of 1 to 150 hours.

19. The device according to claim 16, wherein said controlled thermal treatment comprising heating the annealed borosilicate glass at a temperature of 650-750° C. for a time period of 1 to 150 hours.

20. The device according to claim 16, wherein said controlled thermal treatment comprising heating the annealed borosilicate glass at a temperature of 700-725° C. for a time period of 1 to 150 hours.

21. The device according to claim 17, wherein said time period is 24 to 48 hours.

22. The device according to claim 17, wherein said time period is 48 to 80 hours.

23. The device according to claim 16, wherein said annealed borosilicate glass comprises (based on wt. %):

| | |
|---|---|
| $B_2O_3$ | 15.00-40.00 |
| $SiO_2$ | 45.00-80.00 |
| $R_2O$ | 0.0-20.0 |
| R'O | 0.0-20.00 |
| R''$O_2$ | 0.0-10.00 |
| $Al_2O_3$ | 0.0-10.00 | wherein $R_2O$ is the sum of $Li_2O$, $Na_2O$, $K_2O$, and $Cs_2O$, R'O is the sum of BaO, CaO, MgO, SrO, and ZnO, and R''$O_2$ is the sum of $TiO_2$, $ZrO_2$, and $HfO_2$.

24. The device according to claim 16, wherein said annealed borosilicate glass is an annealed alkali borosilicate glass.

25. The device according to claim 16, wherein said annealed borosilicate glass comprises (based on wt. %): 40-80% $SiO_2$, 5-35% $B_2O_3$ and 1-10% $Na_2O$.

26. The device according to claim 25, wherein said annealed borosilicate glass comprises (based on wt. %): 45-65% $SiO_2$, 20-30% $B_2O_3$ and 2-8% $Na_2O$.

27. The device according to claim 26, wherein said annealed borosilicate glass comprises (based on wt. %): 50-55% $SiO_2$, 25-27% $B_2O_3$ and 5-7% $Na_2O$.

28. The device according to claim 1, wherein said device includes a plurality of optical fibers and each of said optical fibers has one of said Mie scattering optical elements attached to an end thereof.

29. The device according to claim 1, wherein said device comprises a plurality of said optical fibers in the form of an optical fiber bundle, and one of said Mie scattering optical elements is attached to an end of said optical fiber bundle.

30. A process for preparing a device according to claim 1, said process comprising: preparing one of said Mie scattering optical elements by subjecting an annealed glass to a phase separation using a controlled thermal treatment, and optionally subjecting the phase-separated borosilicate glass to an acid leach to create pores and a caustic leach to clean the resultant pores, and attaching the resultant Mie scattering optical element to the end of one of said optical fibers or to an end of a bundle of said optical fibers.

31. The process according to claim 30, wherein said resultant Mie scattering optical element is attached to the end of said one of said optical fibers or to an end of said bundle of said optical fibers by fusion splicing.

32. The process according to claim 30, wherein said resultant Mie scattering optical element is attached to the end of said one of said optical fibers or to an end of said bundle of said optical fibers by an optically clear silicone adhesive.

33. The process according to claim 30, wherein said resultant Mie scattering optical element is attached to the end of said one of said optical fibers or to an end of said bundle of said optical fibers by a nanofoil.

34. A method for dispersing or scattering light transmitted by an optical device comprising an optical fiber and a Mie scattering optical element for dispersing light, said process comprising:

transmitting the light emitted from an end of said optical fiber, through said Mie scattering optical element, whereby said light is dispersed predominantly in the forward direction, said Mie scattering optical element comprising a phase-separated or porous glass having dispersed phase particles with a particle size of 200 to 500 nanometers or pores having a size of 200 to 500 nanometers, at a number density of $10^8$ to $10^{12}$ mm$^{-3}$.

35. The method according to claim 27, wherein said optical device is an optical fiber.

36. The method according to claim 27, wherein said optical device is an optical fiber bundle.

\* \* \* \* \*